US010980984B2

(12) United States Patent
Bennett et al.

(10) Patent No.: US 10,980,984 B2
(45) Date of Patent: Apr. 20, 2021

(54) GUIDEWIRE RETENTION CLIP

(71) Applicant: VIRGINIA COMMONWEALTH UNIVERSITY, Richmond, VA (US)

(72) Inventors: Hilton Bennett, Richmond, VA (US); William Paul Murphy, Richmond, VA (US); Bennett Ward, Midlothian, VA (US); Nathan Minh Le, Richmond, VA (US); Ramya Nandigam, Richmond, VA (US); Sara Um, Richmond, VA (US)

(73) Assignee: VIRGINIA COMMONWEALTH UNIVERISTY, Richmond, VA (US)

( * ) Notice: Subject to any disclaimer, the term of this patent is extended or adjusted under 35 U.S.C. 154(b) by 229 days.

(21) Appl. No.: 15/955,738

(22) Filed: Apr. 18, 2018

(65) Prior Publication Data

US 2018/0304049 A1 Oct. 25, 2018

Related U.S. Application Data

(60) Provisional application No. 62/487,257, filed on Apr. 19, 2017.

(51) Int. Cl.
*A61B 5/00* (2006.01)
*A61M 25/09* (2006.01)
*A61M 25/01* (2006.01)

(52) U.S. Cl.
CPC ............. *A61M 25/09041* (2013.01); *A61M 2025/0177* (2013.01); *A61M 2025/09125* (2013.01); *A61M 2205/18* (2013.01); *A61M 2205/581* (2013.01); *A61M 2205/583* (2013.01)

(58) Field of Classification Search
CPC ............ A61M 25/09; A61M 25/09041; A61M 2025/09125; A61M 2025/0177; A61M 2205/581; A61M 2205/583; A61M 2205/18
USPC ........................................... 600/585
See application file for complete search history.

(56) References Cited

U.S. PATENT DOCUMENTS

| | | | |
|---|---|---|---|
| 2,170,594 A | 8/1939 | Nicholson | |
| 5,507,300 A | 4/1996 | Mukai et al. | |
| 9,205,229 B2* | 12/2015 | Khalaj | A61M 25/0113 |
| 2010/0191152 A1* | 7/2010 | Boutillette | A61M 25/09041 |
| | | | 600/585 |
| 2014/0023788 A1 | 8/2014 | Taboada | |
| 2015/0119702 A1* | 4/2015 | Mulumudi | A61B 5/061 |
| | | | 600/424 |
| 2015/0016516 A1 | 6/2015 | Gallacher et al. | |
| 2018/0117286 A1* | 5/2018 | O'Brien | A61M 5/1418 |

* cited by examiner

*Primary Examiner* — Max F Hindenburg
(74) *Attorney, Agent, or Firm* — W&C IP

(57) ABSTRACT

A guidewire retention clip is provided to prevent the accidental, complete insertion of a guidewire into a patient during various procedures. As provided herein, the guidewire retention clip may include a body having a portion configured to hold a guidewire; a sensor associated with the body configured to detect movement of the guidewire to and from the body; and an audio and/or visual indicator arranged on the body, wherein the audio and/or visual indicator is triggered when the sensor detects movement of the guidewire. Methods of using the guidewire retention clip are also provided.

21 Claims, 11 Drawing Sheets

GUIDEWIRE RETENTION CLIP

CROSS-REFERENCE TO RELATED APPLICATIONS

This application claims benefit of U.S. provisional patent application 62/487,257, filed Apr. 19, 2017, the complete contents of which is hereby incorporated by reference.

FIELD OF THE INVENTION

Embodiments of the invention provide a guidewire retention clip that prevents complete guidewire migration into patients during medical procedures.

BACKGROUND OF THE INVENTION

Guidewires are often used to position and guide the insertion of medical devices, such as a catheter, into a body cavity, such as a blood vessel, of a patient. The guidewire is positioned to allow a catheter to be passed therealong and to follow the path of the guidewire into the patient. The guidewire is thereafter withdrawn and the catheter is ready for further positioning and use.

Millions of patients undergo medical procedures using guidewire, such as central venous cannulation, every year. Placing a central venous catheter (CVC) allows medical interventions such as fluid resuscitation, potent drug therapy, embolization, stent placement, cardiac catheterizations, and many major surgeries.

To place a CVC, the 60-year-old Seldinger technique is the standard of care. A short needle is inserted into the target vessel, then a guidewire is then placed through the needle into the vessel, and then the needle is removed. Then, a dilator is placed to open the vessel entryway and then a catheter is threaded over the guidewire and guided into the vein by the wire. Once the catheter is in place, the guidewire is removed.

While the wire is in the vein, care must be taken to prevent its accidental, total insertion. Since this depends solely on human vigilance, errors happen. Every year, over a thousand guidewires are lost inside patients nationwide, often due to practitioner distraction or fatigue. While retained guidewires are recognized as a major safety issue, no effective solution has been presented. In addition to the significant cost of retrieval procedures, litigation, and negative publicity, retained wires expose patients to risks of infection, vessel perforation, stroke, cardiac arrhythmia, and death.

SUMMARY OF THE INVENTION

The guidewire retention clip, according to embodiments of the invention, is a device that prevents the complete insertion of guidewire into a patient. The clip itself acts as a physical block against total wire insertion. Further, the clip includes a visual and/or auditory alarm that alerts the user when the guidewire is released from the clip.

In one aspect of the invention, the clip comprises a body having a portion configured to hold a guidewire; a sensor associated with the body configured to detect movement of the guidewire to and from the body; and an audio and/or visual indicator arranged on the body, wherein the audio and/or visual indicator is triggered when the sensor detects movement of the guidewire.

In some embodiments, the clip comprises a body having two elongated members, wherein the ends of the two elongated members are configured to take a closed position or an open position, wherein an end of each elongated member are together configured to hold a guidewire in the closed position and are configured to release a guidewire in the open position; a pivoting means on each of the two elongated members, wherein the pivoting means is configured to place the ends of the two elongated members in the open position when the body is compressed; a sensor on an inner surface of at least one of the elongated members configured to detect movement of the guidewire; and an audio and/or visual indicator arranged on the body, wherein the audio and/or visual indicator is triggered when the sensor detects movement of the guidewire.

In other embodiments, the clip comprises a housing having a cavity for insertion of a guidewire; a piston within the housing configured to move an inner surface of the cavity into a closed position or an open position; a spring abutting one end of the piston; a handle connected to the piston; a sensor on an inner surface of the cavity configured to detect movement of the guidewire; and an audio and/or visual indicator arranged on or in the housing, wherein the audio and/or visual indicator is triggered when the sensor detects movement of the guidewire.

In some embodiments, a kit comprising guidewire and a clip as described herein attached to the guidewire is provided.

Another aspect of the invention provides a method for inserting a catheter into a body lumen of a patient, comprising the steps of: placing a guidewire having a guidewire retention clip attached into the body lumen of the patient; releasing the guidewire from the clip to allow the passage of the catheter over the guidewire; attaching the clip to the guidewire; inserting the catheter into the body lumen; removing the guidewire with the clip attached from the blood vessel; and securing the catheter in place.

Additional features and advantages of the invention will be set forth in the description below, and in part will be apparent from the description, or may be learned by practice of the invention. The advantages of the invention can be realized and attained by the exemplary structure particularly pointed out in the written description and claims hereof as well as the appended drawings.

DETAILED DESCRIPTION

Embodiments of the invention provide a guidewire retention clip having a body with a portion configured to hold a guidewire; a sensor associated with the body configured to detect movement of the guidewire to and from the body; and an audio and/or visual indicator arranged on the body, wherein the audio and/or visual indicator is triggered when the sensor detects movement of the guidewire.

In some embodiments, the body includes two elongated members. In some embodiments, the body is substantially U-shaped. The ends of the two elongated members are configured to take a closed position or an open position, wherein an end of each elongated member are together configured to hold a guidewire in the closed position and are configured to release a guidewire in the open position.

Figure 1A:
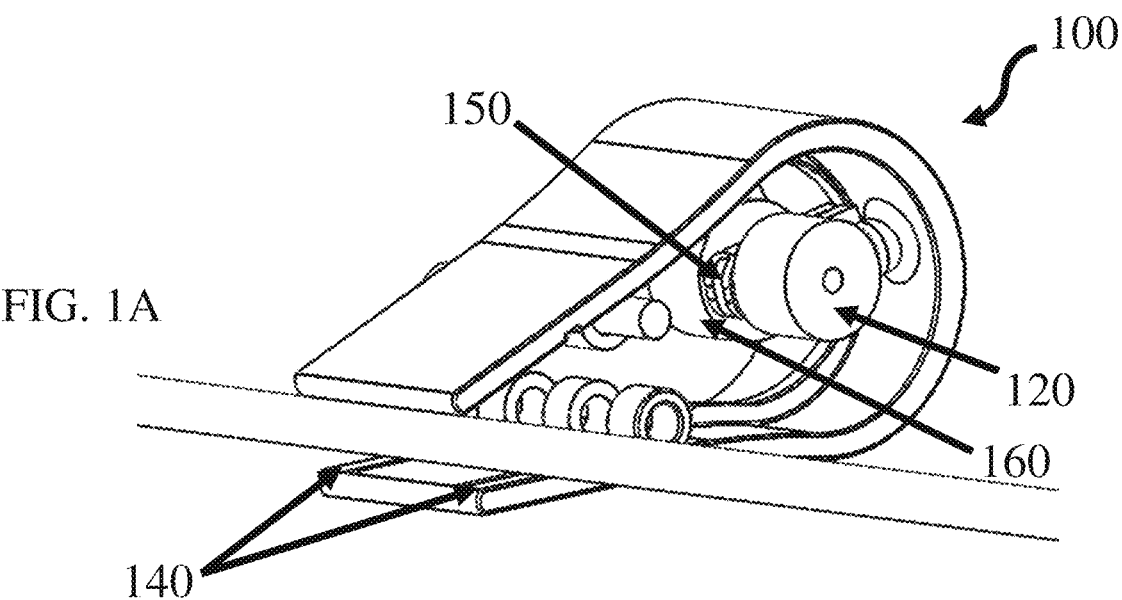
FIG. 1A is a side view of a guidewire retention clip according to some embodiments of the disclosure.
Figure 1B:
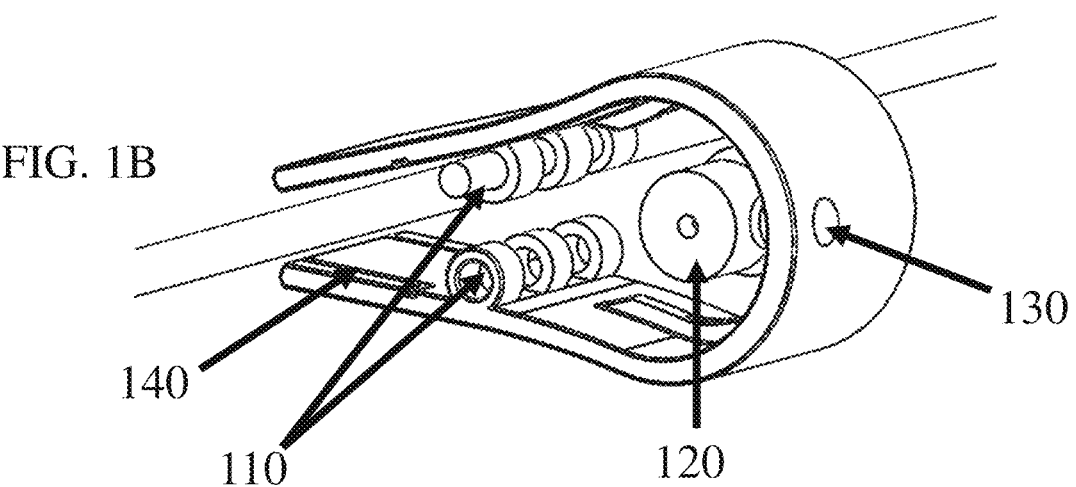
FIG. 1B is an alternative view of a guidewire retention clip according to some embodiments of the disclosure.

With reference to FIGS. 1A and 1B showing a clip 100 in the closed position attached to a guidewire, the clip 100 may include a pivoting means 110 on an inner surface of at least one of the two elongated members. In some embodiments, the pivoting means comprises one or more projections of any shape that causes the two elongated members to come in contact upon compression of the U-shaped body about a midpoint. Examples of such pivoting means are known in the art and may be found in commercially available fishing line release clips, e.g. the Scotty® Power Grip Plus Release clip. Compression of the U-shaped body about the pivoting means configures the ends of the two elongated members in the open position. As shown in FIG. 1B, the downward arrow represents compression about the midpoint while the upward arrow represents the opening of the ends of the elongated members.

Figure 2:
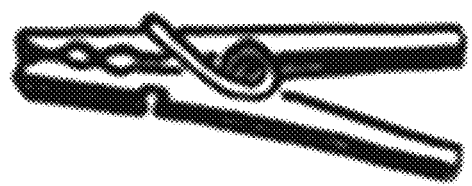
FIG. 2 is an exemplary body shape of a guidewire retention clip according to some embodiments of the disclosure.

With reference to FIG. 2, in some embodiments, the clip 100 may include operate similarly to a clothespin for example. Thus, in some embodiments, the pivoting means joins the two elongated members whether the clip is in the open or closed position and may include, e.g. a spring. The open position is obtained upon compression of the clip body at one end of the elongated members.

The clip 100 has a size that is sufficient for a user to easily handle during use, e.g., to compress the body of the clip when removing the clip from the guidewire. In some embodiments, the clip is at least one-half inch in length and one-half inch in width. In some embodiments, the clip is at least about two inches in length and at least about a half inch in width. In some embodiments, the clip is at least about four inches in length and at least about a half inch in width. The body of the clip may be fabricated from any material suitable for use in a medical environment, such as plastic or metal materials. The elongated members of the body may have a filleted cap rather than a sharpened point, and conjoining feet. When the body is compressed, e.g. at the midpoint or at an end of the body, the feet open and when decompressed, it retains a closed foot position. When closed, the clip can be used to grip the guide wire used in catheterization surgical procedures (e.g. insertion of a central venous catheter), preventing the wire from accidentally being inserted in its entire length into the patient's body. In some embodiments, the feet provide at least about 4 oz of pressure across the closed surfaces in order to inhibit guidewire movement without deforming or damaging the guidewire. In some embodiments, there is at least about 8 oz of pressure across the closed surfaces.

Figure 3A:
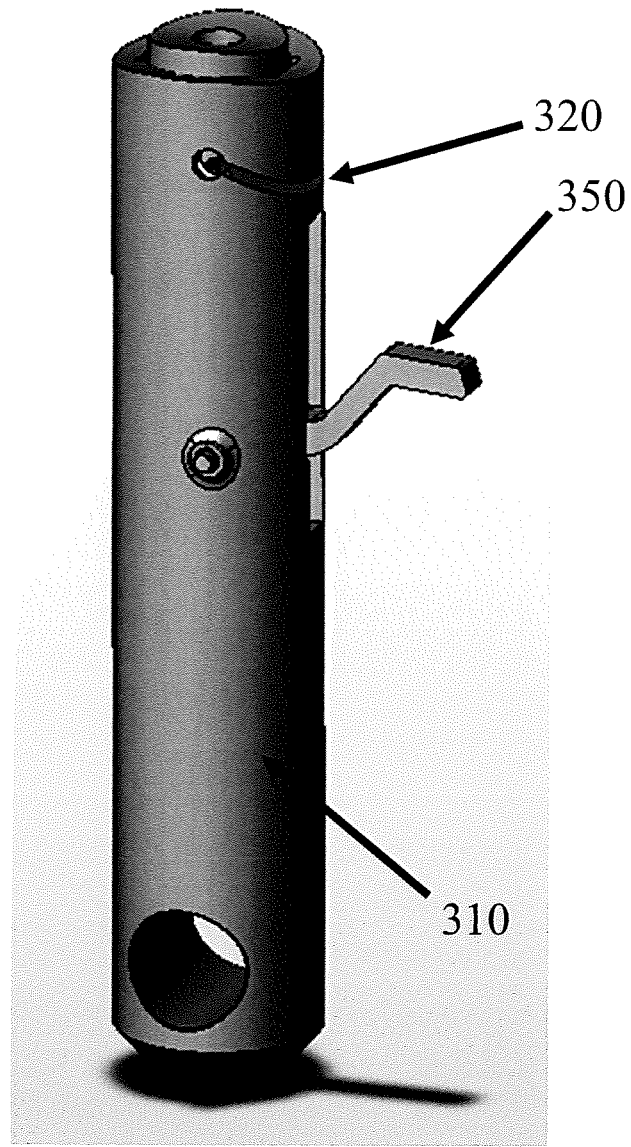
FIG. 3A is an exemplary guidewire retention clip according to some embodiments of the disclosure.
Figure 3B:
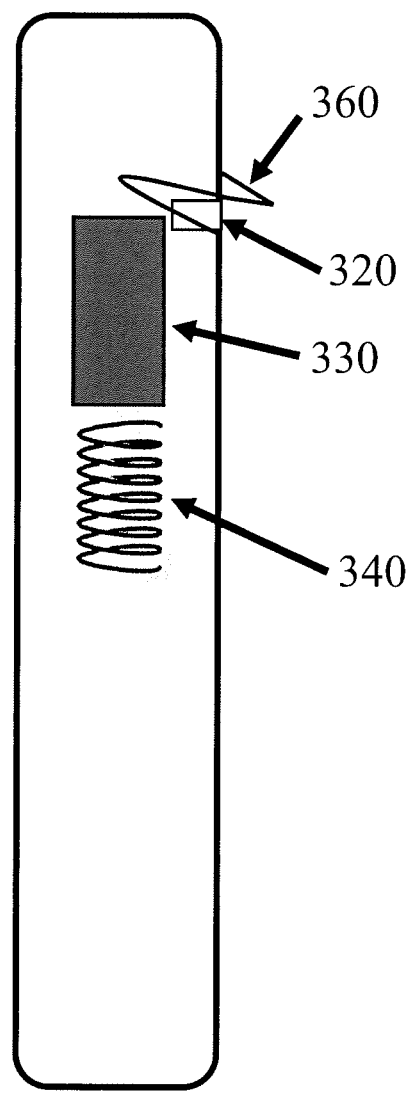
FIG. 3B is a cut away diagram of an exemplary guidewire retention clip according to some embodiments of the disclosure.
Figure 3C:
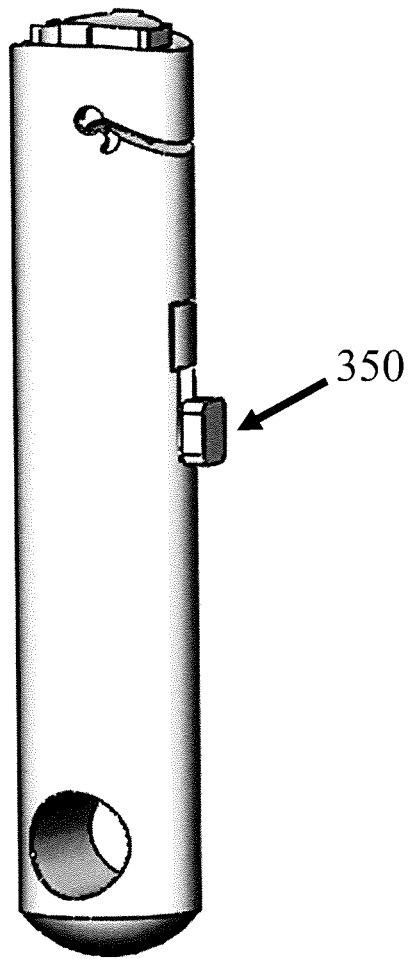
FIG. 3C is an exemplary guidewire retention clip according to some embodiments of the disclosure.
Figure 3D:
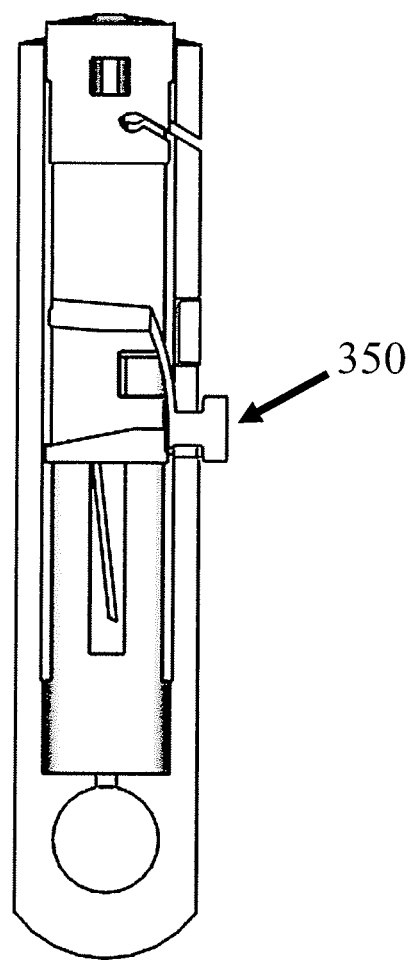
FIG. 3D is a cut away diagram of an exemplary guidewire retention clip according to some embodiments of the disclosure.
Figure 3E:
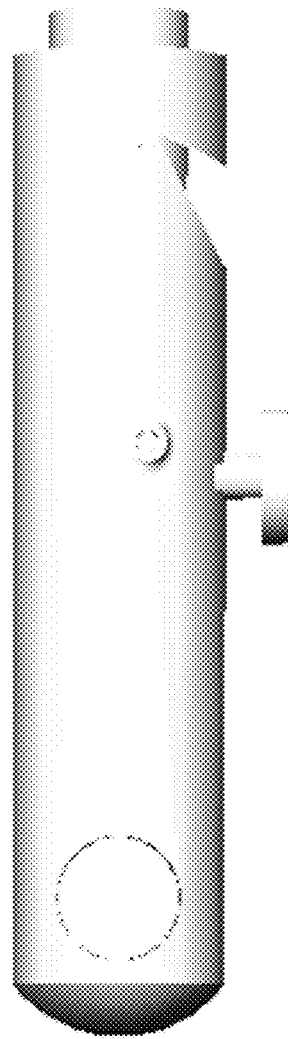
FIG. 3E is an exemplary guidewire retention clip according to some embodiments of the disclosure.
Figure 3F:
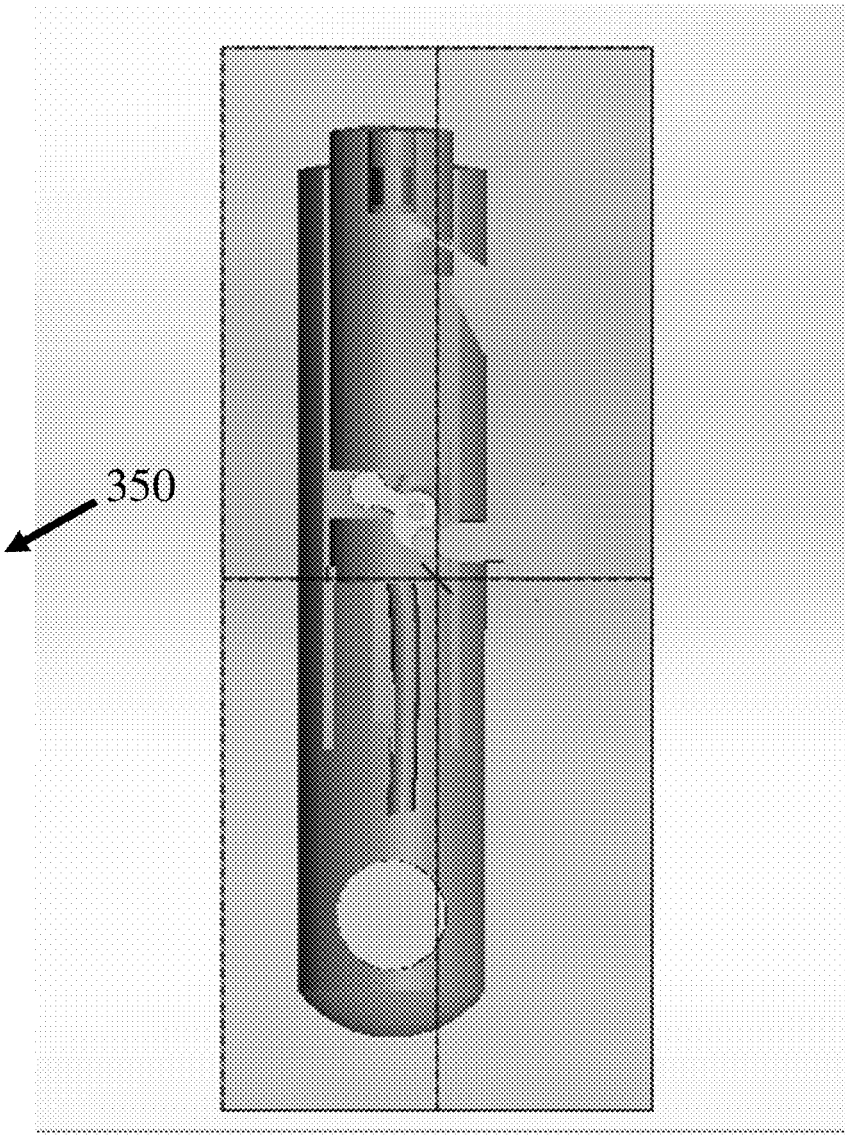
FIG. 3F is a cut away diagram of an exemplary guidewire retention clip according to some embodiments of the disclosure.
Figure 4A:
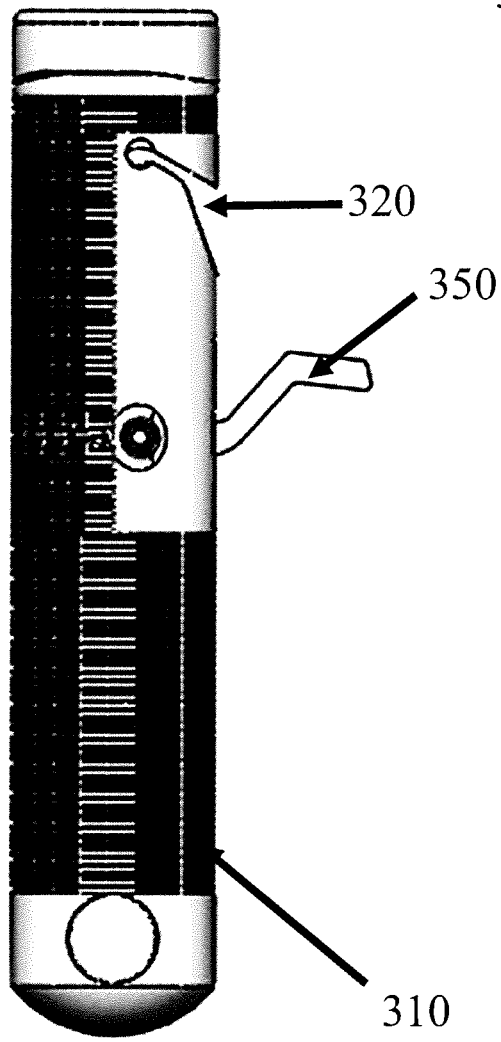
FIG. 4A is an exemplary body shape is of a guidewire retention clip according to some embodiments of the disclosure.
Figure 4B:
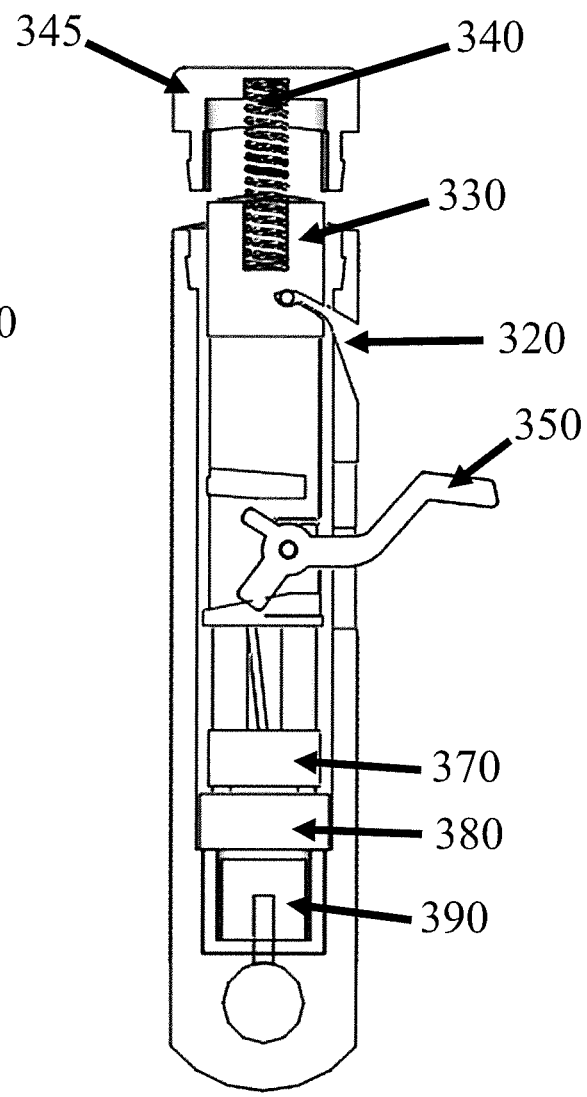
FIG. 4B is a cut away diagram of an exemplary guidewire retention clip according to some embodiments of the disclosure.
Figure 4C:
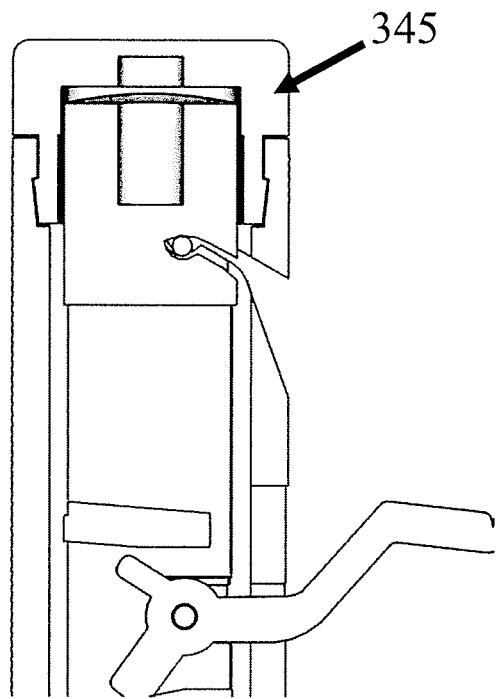
FIG. 4C is a cut away diagram of an exemplary guidewire retention clip according to some embodiments of the disclosure.
Figure 4D:
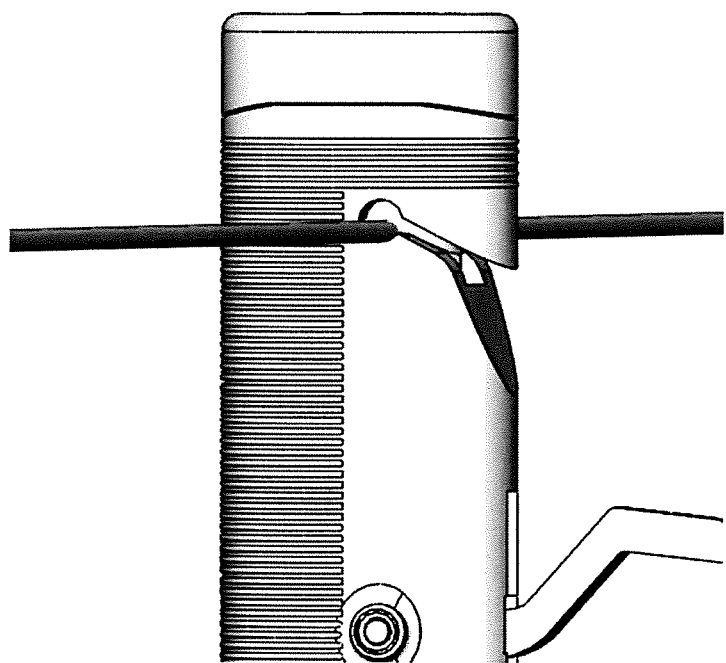
FIG. 4D is an exemplary guidewire retention clip according to some embodiments of the disclosure attached to a guidewire.

With reference to FIGS. 3A, 3B, 4A, 4B, 4C, 4D, 4E, and 4F, in some embodiments, the clip comprises a housing 310 having a cavity 320 for insertion of a guidewire. In some embodiments, the cavity 320 extends inward to about half the circumference of the housing 320. The cavity 320 may, e.g., be in the shape of an elongated V or have "check-mark" shape. In some embodiments, the housing 310 also includes a lip 360 extending from an outer surface of the housing 310 adjacent to the cavity 320. In some embodiments, the opening of the cavity is enlarged (FIGS. 4A-F). The shape of the cavity 320 and, if present, the lip 360 helps the practitioner guide the guidewire into the back of the cavity 320 to the wire locking location formed by an inner surface of the cavity (FIG. 4D). For example, a practitioner may slide the guidewire along the housing until the guidewire is "hooked" into the cavity. A handle 350, e.g. a lever (FIG. 3A), a sliding mechanism (FIGS. 3C and 3D), or a push button mechanism (FIGS. 3E and 3F) is provided to actuate a piston 330 abutting a spring 340 within the housing 310 that causes an inner surface of the cavity 320 to open and close around a guidewire.

In some embodiments, the clip includes a cap 345 at the top of the housing 310 that compresses the spring 340 when in the closed position (FIGS. 4B and 4C). The cap 345 may have a hook and latch comprising protruding arms that latch into the body of the clip. When the cap 345 is latched, the spring 340 creates a closed position by forcing the pendulum of the lever 350 down (lever arm up) so that the clip remains closed under a pressure. The lever 350 arm may then be pushed down in order to unlatch the cap and provide an open position of the clip. In some embodiments, the spring 340 could function under conditions of 1 oz up to about 10 lbs. In some embodiments, the spring 340 is rated at 2.6 lbs.

Figure 4E:
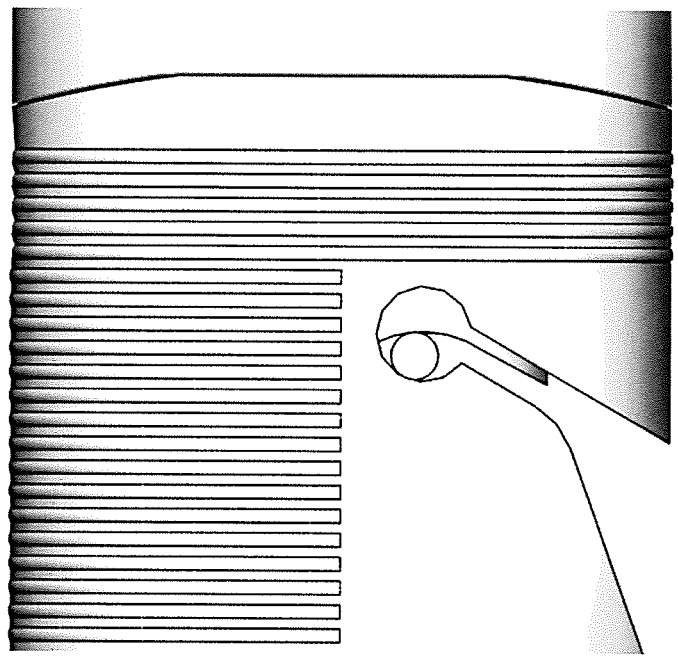
FIG. 4E is a close-up view of an exemplary guidewire retention clip attached to a guidewire in the closed position.
Figure 4F:
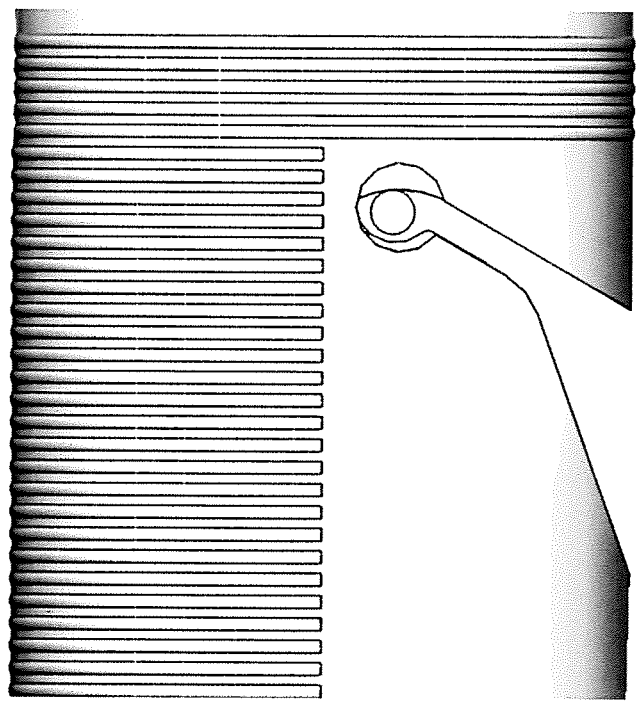
FIG. 4F is a close-up view of an exemplary guidewire retention clip in the open position.
Figure 4G:
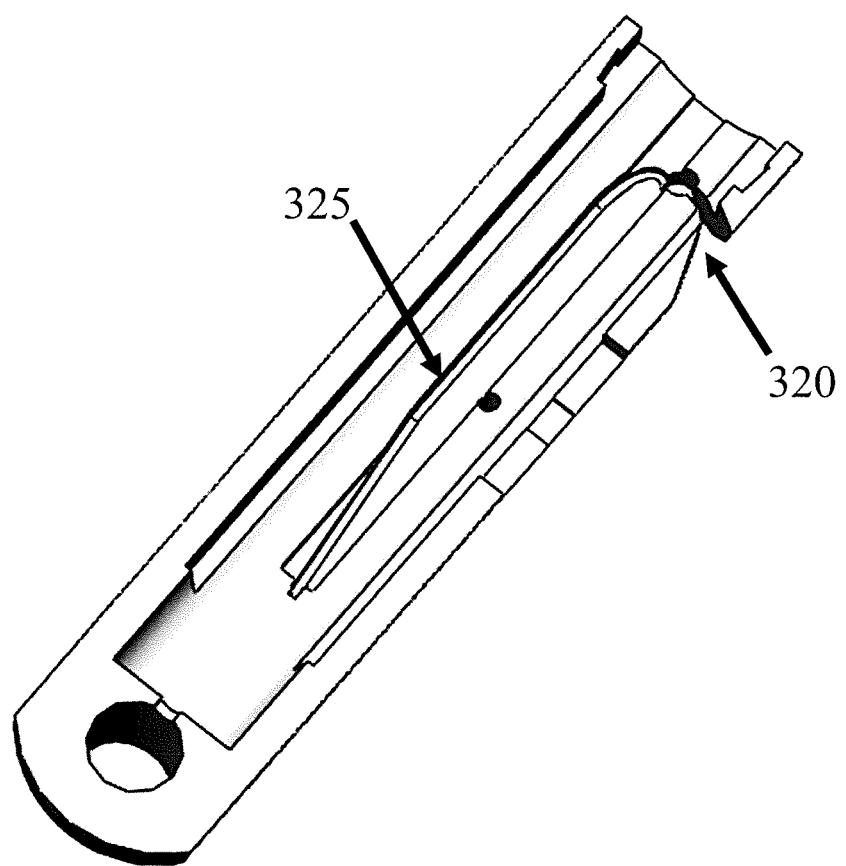
FIG. 4G is a cut away diagram of an exemplary guidewire retention clip according to some embodiments of the disclosure.

FIG. 4E shows the cavity 320 holding a guidewire in the closed position and FIG. 4F shows the open position in which the guidewire can be released. FIG. 4G shows the path 325 of a contact wire of the sensor extending from the inner surface of the cavity where the contact wire contacts a guidewire to the location of the circuit.

The shape of the handle 350 would allow the handle to be actuated using only a practitioner's thumb on either hand. In some embodiments, the default position of an inner surface of the cavity 320 is closed. Movement of the handle 350 causes the piston 330 to compress against the spring 340 and allows an inner surface of the cavity 320 to open.

The housing 310 of the clip may also include a battery 370, circuit 380, and buzzer 390 as described herein.

In some embodiments, movement of the handle 350 is accompanied by an auditory click and/or tactile feedback. Thus, pushing or sliding the handle 350 down (or pushing the button handle 350 in), e.g. to grasp (or release) the wire and pushing or sliding the handle 350 up (or releasing the button handle 350 or pulling the button handle 350 out), e.g. to lock the wire in place is accompanied by a tactile and/or audible signal when the task is accomplished. In some embodiments, the handle 350 cannot be locked in a "down" (or "in") position (where the cavity is open) and thus a tactile and/or audible signal is only provided when the handle 350 is moved up (or when the handle 350 is released or pulled out) to grasp the wire.

In some embodiments, the housing 310 is cylindrical. In other embodiments, the outer surface of the housing 310 has an oval, angular, or cubical shape to reduce rolling of the clip when grasped or placed on a surface. In some embodiments, at least a portion of the outer surface of the housing 310 is ridged or rough in order to provide a more secure grip (FIG. 4A). In some embodiments, at least a portion of the outer surface of the housing 310 has a rubberized coating or texture. In some embodiments, the housing is substantially or hermetically sealed to inhibit or prevent blood or other liquids from entering the device.

The housing 310 has a size that is sufficient for a user to easily handle during use. In some embodiments, the housing is at least about 2 cm in diameter. The housing 310 may be fabricated from any material suitable for use in a medical environment, such as plastic or metal materials. In some embodiments, an inner surface of the cavity 320 provides at least about 4 oz of pressure across the closed surfaces in order to inhibit guidewire movement without deforming or damaging the guidewire. In some embodiments, there is at least about 8 oz of pressure across the closed surfaces.

The clip may contain a digital alarm feature housed generally in or about the body or housing of the clip. Such an alarm would activate once the clip is released from the wire and would continue to sound and/or provide visual signals until the clip is again closed about the wire. The alarm would provide a signal to the user that the wire would need to be secured thus providing an extra layer of safety regarding preventing losing of the wire inside the patient.

The audible signal may be a chirp, beep, siren, vibration, or other sound signal, such as a buzzer 120. The visual signal or indicator 130 may be, e.g. a strobe, flash, LED light or other light emitter. In some embodiments, a light indicator 130 flashes or provides a steady green light when clipped and flashes or provides a steady red light when removed from the wire. In other embodiments, the light indicator 130 is only activated, i.e. flashing or providing steady light, when the clip is removed from the guidewire. In some embodiments, the release alarm emits both an audible signal and visual signal. In some embodiments, the release alarm emits a tactile signal, such as vibration.

The release alarm may alternatively, or in conjunction with generating one or both of audible and visual signals, generate a communication signal in response to the guidewire being released from the clip. The communication signal may be via a wireless signal, such as Bluetooth, RF, infrared or other wireless communication for triggering an alarm on a nearby or remote receiver, such as a computer, tablet, or mobile phone.

The digital release alarm may include a battery 160 and an electronic circuit (such as a printed circuit board) 150 which emits at least one of an electrically generated audible signal, an electrically generated visual (e.g., light) signal, or a communication signal in response to the clip moving from the closed position and/or the clip being in the open position. The signal emitted by the release alarm may be in response to motion and/or position of the guidewire. The circuit may optionally include a logic circuit that controls the mode of the release alarm, which may also include the sound, light, and/or communication signal that is created. For example, in some embodiments, the nature or intensity of the alarm may change over the time period that the guidewire is released from the clip, e.g. by using different audio signals, different color lights, different light flashing rates, and the like. For example, the intensity of the audio signal may slowly increase the longer the clip is not attached to the guidewire. It is contemplated that simpler designs may omit the logic circuit and may have the sensor 140 directly interfaced with the release alarm.

Figure 5A:
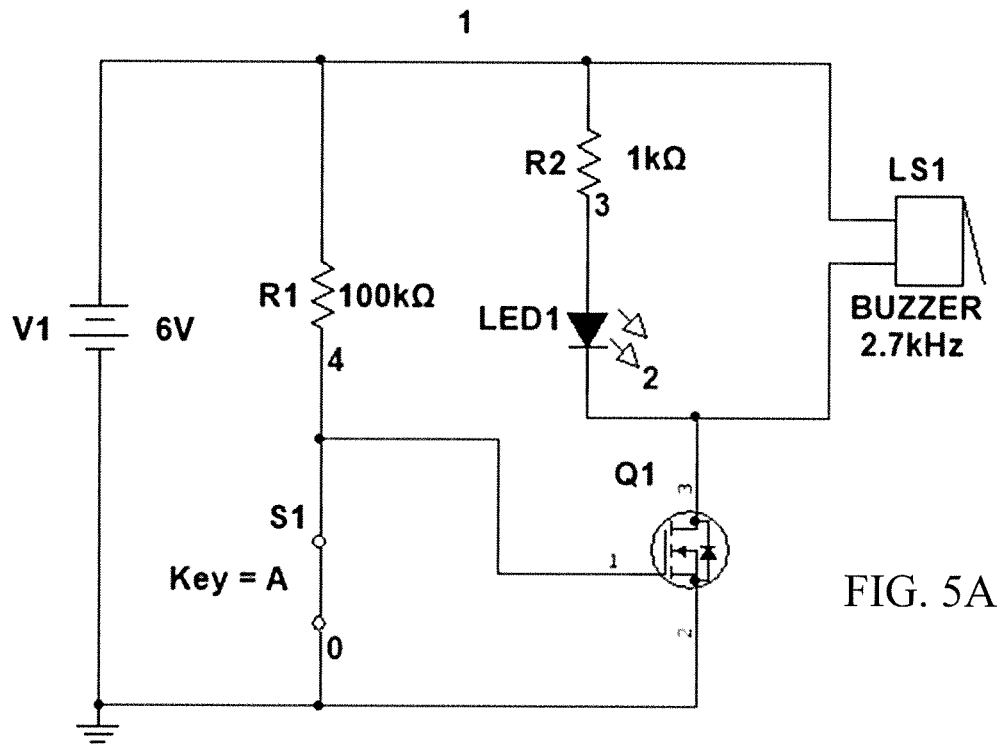
FIG. 5A is a diagram of an exemplary circuit when the contact points (Key A) are connected according to some embodiments of the disclosure.
Figure 5B:
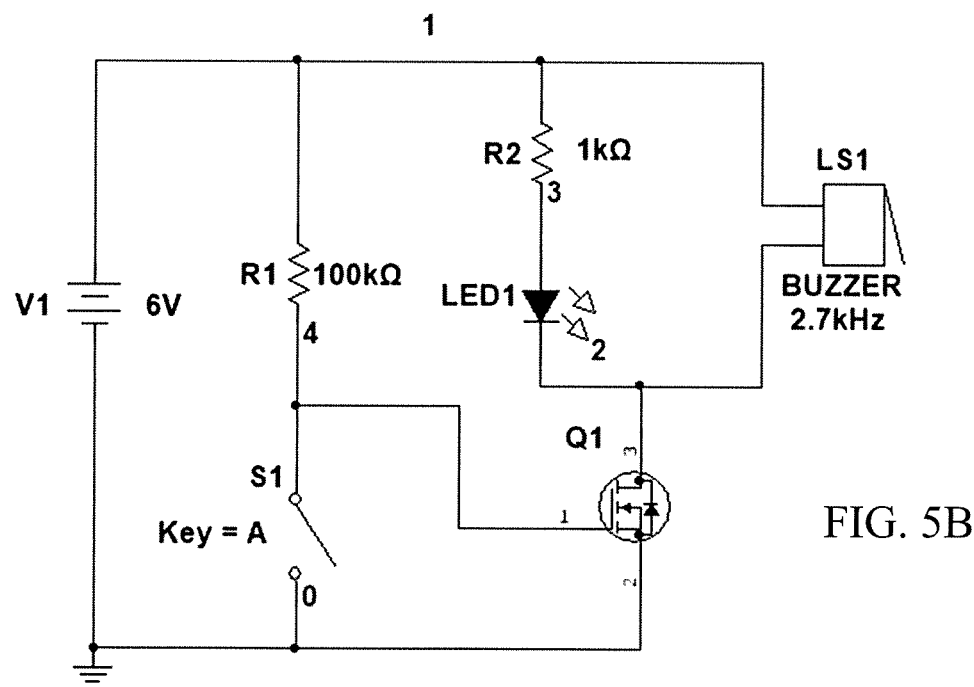
FIG. 5B is a diagram of an exemplary circuit when the contact points (Key A) are not connected according to some embodiments of the disclosure.

With reference to FIGS. 5A and 5B, in some embodiments of the invention, the circuit comprises a metal-oxide-semiconductor field-effect transistor (MOSFET) that functions as a switch. In some embodiments, an enhancement n-channel MOSFET type is used which is visually represented by broken lines next to the labeled port 1. This type infers "NORMALLY-OFF" when the circuit is ON. The circuit may include a power source (e.g., a battery), a buzzer and/or an LED (auditory or visual alarm or both). In some embodiments, the circuit closes when a guidewire is attached to the clip and thus there is no current flowing through the wire or the current is negligible. The MOSFET references as Q1 in FIG. 5A. Pin 1 is the GATE terminal, pin 2 is the SOURCE terminal, and pin 3 is the DRAIN terminal. In this case, zero watt of power is dissipated since the GATE and SOURCE terminal are powered with the same voltage, which activated "NORMAL OFF" state of the MOSFET. This means that there will be no current flows through the DRAIN terminal, where the loads (LED and buzzer) are connected to, hence the circuit is off. Therefore, as long as a guidewire is in contact with these two contact points, this circuit will not draw any power. In case the guidewire is not connected to the contact points, represented by the open switch (key A) if FIG. 5B, there is a potential difference between the SOURCE terminal (pin 1) and the GATE terminal (pin 2). This difference in voltage causes the current to flow through the DRAIN terminal (pin 3) and activates the buzzer and LED. Consequently, the buzzer goes off and the LED lights up to notify the practitioner that the guidewire is in the danger state of being lost.

The sensor 140 is provided on an inner surface at the end of at least one of the elongated members or on an inner surface of the cavity 320 for detecting the presence and/or movement of the guidewire. In some embodiments, the sensor 140 may be an electrode, a proximity sensor, a limit switch, a hall-effect sensor, an encode accelerometer, or another sensor suitable for detecting an indicia of the position and/or movement of the guidewire. In some embodiments, the sensor 140 only detects movement of the guidewire to and from the body of the clip.

In some embodiments, a kit containing a clip as described herein is provided. For example, a clip according to the disclosure is pre-attached to guidewire in a kit such as a catheterization kit or central line cannulation kit. Thus, the clip may also be incorporated into existing commercially available kits for various medical procedures.

In some embodiments, the kit contains a clip attached to a piece of conductive material bridging the contact points of the sensor, thus disarming the alarm as if a guidewire were attached. The conductive material may be metal, metallic paper, coated plastic, etc. and would prevent the battery from discharging during storage. In some embodiments, the conductive material is attached or a part of the packaging and thus must be removed when the packaging is opened. It is also contemplated that a means such as a barb or spring-loaded flap is provided to prevent reuse once initially withdrawn.

Figure 6:
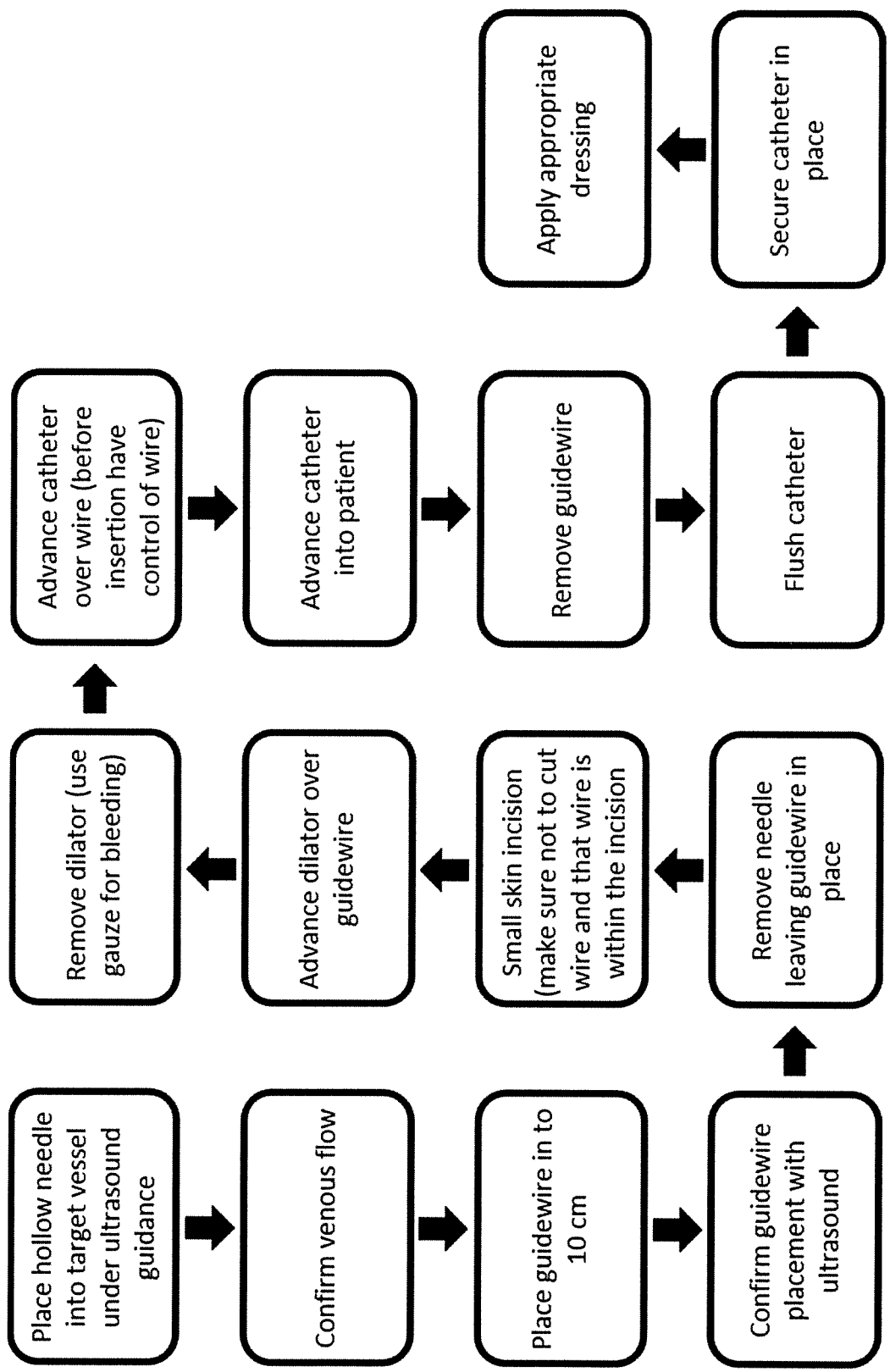
FIG. 6 is an exemplary flowchart of the Seldinger technique.
Figure 7:
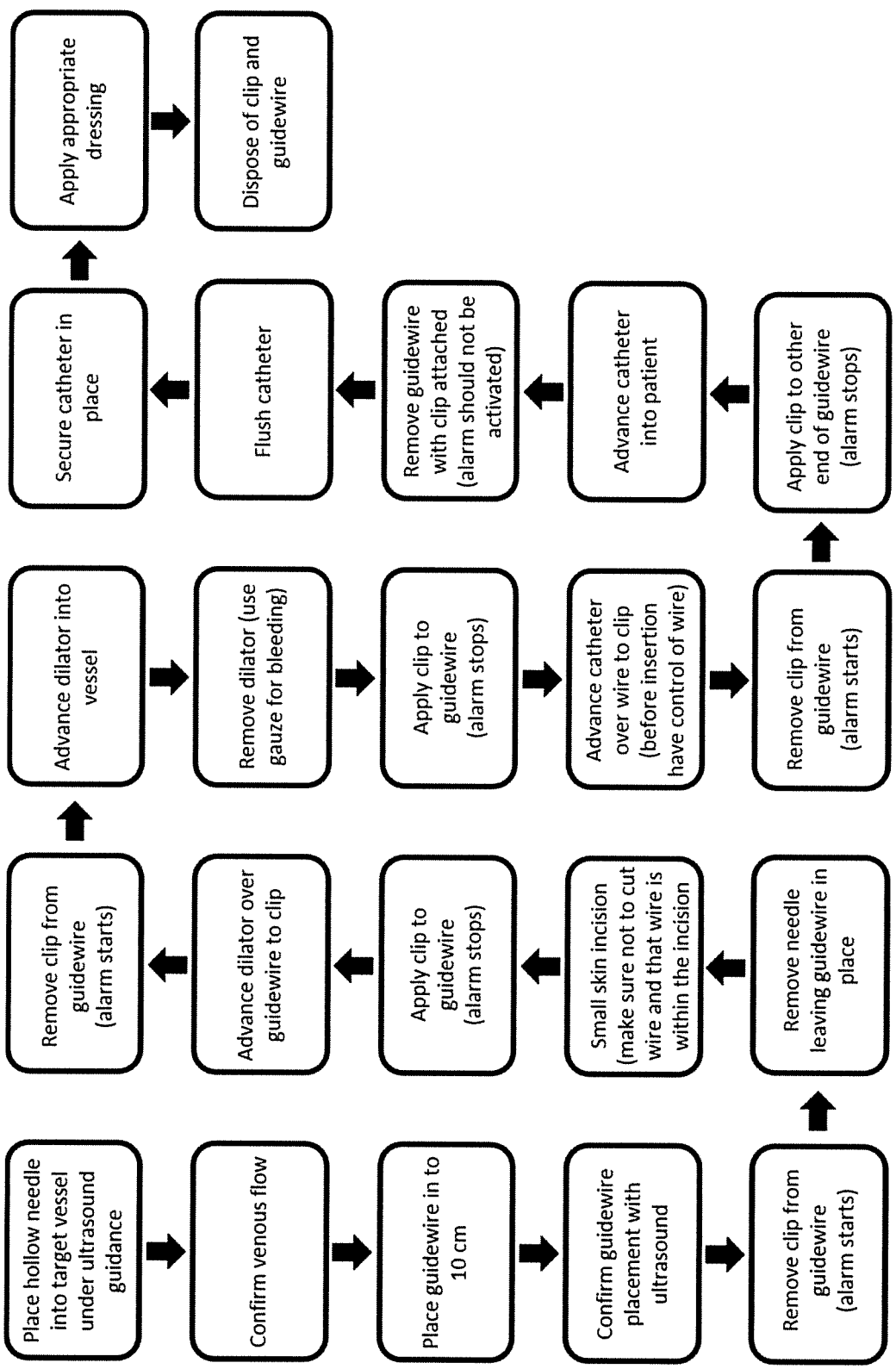
FIG. 7 is an exemplary flowchart of a modified Seldinger technique using a guidewire retention clip according to some embodiments of the disclosure.

As is known in the art, the Seldinger technique is commonly used to insert catheters (see FIG. 6). This method uses a series of guidewire placements into blood vessels to both facilitate penetration of catheters into the vasculature and also to guide the placement of said catheters at the exact location where a medical procedure (e.g., stent placement, cardiac ablation, etc.) would be performed. In some methods of the present disclosure, a clip as described herein may be used in a modified Seldinger method to prevent the accidental insertion of the entire guidewire. An example of such a method is provided in FIG. 7. In some embodiments, a method for inserting a catheter into a body lumen of a patient, comprises the steps of: placing a guidewire having a guidewire retention clip attached into the body lumen of the patient, releasing the guidewire from the clip to allow the passage of the catheter over the guidewire, attaching the clip to the guidewire, inserting the catheter into the body lumen, removing the guidewire with the clip attached from the blood vessel, and securing the catheter in place.

In some embodiments of the method of the invention, the clip is only applied to the wire at the point of insertion proximal to the patient. In other embodiments, a longer process is used in which the clip is applied to both the proximal and distal wire ends and thus the clip is present on the wire during each stage of the catheterization procedure.

While guidewires are more commonly used to cannulate blood vessels such as a vein, artery, or capillary, other body lumens including a lymphatic vessel, biliary tree, etc. can also be cannulated and embodiments described herein can be used to prevent guidewire migration in systems and methods thereof, and for that matter, any procedure in which a guidewire is used to deliver a medical or non-medical device. A clip as provided herein may be used in procedures including, but not limited to, stent placement, central venous cannulation, fluid resuscitation, cardiac ablation, cardiac catheterization, embolization, and hemodialysis.

One common type of catheter inserted over a guidewire is a central venous catheter, which is typically inserted via an internal jugular, subclavian, axillary, or femoral vein approach. Another type of catheter is a triple lumen dialysis catheter which is used for hemodialysis treatment and could also be entered in a similar fashion in the femoral vein or internal jugular vein, for example. Some non-limiting examples of dialysis catheters that can be used or modified for use herein include Mahurkar™ or Quinton™ catheters, or tunneled catheters such as Hickman™ or Groshong™ catheters for example. In some embodiments, the catheter could be utilized for right or left heart catheterization, such as a Swan-Ganz™ catheter for example. In some embodiments, the catheter could be a central venous catheter (either centrally or peripherally inserted) such as the ARROW® line of catheters manufactured by Teleflex Inc. (Limerick, Pa.).

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A guidewire retention clip, comprising:
a body having a portion configured to retain a guidewire;
a sensor associated with the body configured to detect presence or absence of the guidewire in the body; and
an audio and/or visual indicator arranged on the body, wherein the audio and/or visual indicator is triggered when the sensor detects the absence of the guidewire.

2. The guidewire retention clip of claim 1, wherein attachment of the guidewire to the clip closes a circuit associated with the sensor.

3. The guidewire retention clip of claim 1, wherein
the portion of the body has two elongated members, wherein the ends of the two elongated members are configured to take a closed position or an open position, wherein an end of each elongated member are together configured to retain a guidewire in the closed position and are configured to release a guidewire in the open position;
the sensor is on an inner surface of at least one of the elongated members; and
wherein the clip further comprises a pivoting means on each of the two elongated members, wherein the pivoting means is configured to place the ends of the two elongated members in the open position when the body is compressed.

4. The guidewire retention clip of claim 3, wherein the body is substantially U-shaped and compression about the pivoting means configures the ends of the two elongated members in the open position.

5. The guidewire retention clip of claim 3, wherein compression at the ends of the two elongated members opposite the ends configured to hold the guidewire configures the ends of the two elongated members in the open position.

6. The guidewire retention clip of claim 1, wherein the audio and/or visual indicator is arranged in a cavity of the body.

7. The guidewire retention clip of claim 1, wherein the clip includes both an audio and visual indicator.

8. The guidewire retention clip of claim 1, wherein the sensor is an electrode.

9. The guidewire retention clip of claim 1, further comprising a battery arranged on the body.

10. A kit comprising:
   a guidewire; and
   a guidewire retention clip attached to the guidewire, wherein the clip comprises:
      a body having a portion configured to retain a guidewire;
      a sensor associated with the body configured to detect presence or absence of the guidewire in the body; and
      an audio and/or visual indicator arranged on the body, wherein the audio and/or visual indicator is triggered when the sensor detects the absence of the guidewire.

11. The kit of claim 10, wherein the audio and/or visual indicator arranged in a cavity of the body.

12. The kit of claim 10, wherein the clip includes both an audio and visual indicator.

13. The kit of claim 10, wherein the sensor is an electrode.

14. The kit of claim 10, wherein the clip further comprises a battery arranged on the body.

15. A method for inserting a catheter into a body lumen of a patient, comprising the steps of:

placing a guidewire having a guidewire retention clip attached to the guidewire into the body lumen of the patient, wherein the clip comprises:
   a body having a portion configured to retain a guidewire;
   a sensor associated with the body configured to detect presence or absence of the guidewire in the body; and
   an audio and/or visual indicator arranged on the body, wherein the audio and/or visual indicator is triggered when the sensor detects the absence of the guidewire;
releasing the guidewire from the clip to allow the passage of the catheter over the guidewire;
re-attaching the clip to the guidewire;
inserting the catheter into the body lumen;
removing the guidewire with the clip attached from the blood vessel; and
securing the catheter in place.

16. The method of claim 15, wherein the patient is undergoing stent placement, central venous cannulation, fluid resuscitation, cardiac ablation, cardiac catheterization, embolization, or hemodialysis.

17. The guidewire retention clip of claim 1, wherein the body comprises a housing having a cavity for insertion of a guidewire, the sensor is on an inner surface of the cavity, and wherein the clip further comprises:
   a piston within the housing configured to move an inner surface of the cavity into a closed position or an open position;
   a spring abutting one end of the piston; and
   a handle connected to the piston.

18. The guidewire retention clip of claim 17, further comprising a lip extending from an outer surface of the housing adjacent to the cavity.

19. The guidewire retention clip of claim 17, wherein an outer surface of the housing is ridged.

20. The guidewire retention clip of claim 17, wherein the clip includes both an audio and visual indicator.

21. The guidewire retention clip of claim 17, wherein the sensor is an electrode.

* * * * *